United States Patent [19]

Lauffer

[11] Patent Number: 4,880,008

[45] Date of Patent: Nov. 14, 1989

[54] VIVO ENHANCEMENT OF NMR RELAXIVITY

[75] Inventor: Randall B. Lauffer, Boston, Mass.

[73] Assignee: The General Hospital Corporation, Boston, Mass.

[21] Appl. No.: 860,540

[22] Filed: May 7, 1986

Related U.S. Application Data

[63] Continuation-in-part of Ser. No. 731,841, May 8, 1985.

[51] Int. Cl.$^4$ ............................................... A61K 49/00
[52] U.S. Cl. ......................................... 128/654; 424/9
[58] Field of Search ..................... 128/653, 654; 424/2, 424/9

[56]     References Cited

U.S. PATENT DOCUMENTS

| | | | |
|---|---|---|---|
| 4,472,509 | 9/1984 | Gansow et al. | 424/9 |
| 4,615,879 | 10/1986 | Runge et al. | 128/653 |
| 4,647,447 | 3/1987 | Gries | 424/9 |

FOREIGN PATENT DOCUMENTS

| | | | |
|---|---|---|---|
| 8633082 | 1/1983 | Australia . | |
| 0133603 | 2/1984 | European Pat. Off. | 424/9 |
| 0169299 | 1/1986 | European Pat. Off. | 424/9 |
| 2606721 | 9/1976 | Fed. Rep. of Germany . | |
| 3129906 | 2/1983 | Fed. Rep. of Germany . | |
| 85/02272 | 7/1985 | World Int. Prop. O. | 424/9 |
| 85/05554 | 12/1985 | World Int. Prop. O. | 424/9 |
| 86/01410 | 3/1986 | World Int. Prop. O. | 424/9 |
| 86/02352 | 4/1986 | World Int. Prop. O. | 424/9 |

OTHER PUBLICATIONS

Haddock et al., Proc. Soc. Exptl. Biol. Med., 120:663, (1965).
Bagley et al., Proc. Soc. Exptl. Biol. Med., 127:798, (1968).
Moerlein et al., In. J. Nucl. Med. Biol., 8:277, (1981).
Pecoraro et al., Inorg. Chem., 21:2209, (1981).
Unger et al., "Magnetic Resonance Imaging Using Gadolinium Labeled Monoclonal Antibody", in *Invest. Radiology*, vol. 20, Oct. 1985, pp. 693–700.
Weinmann et al., "Characteristics of Gadolinium-DTPA Complex: a Potential NMR Contrast Agent", in *AJR*, Mar. 1984, pp. 619–624.
Chen et al., "Paramagnetic Metalloporphyrins as Potential Contrast Agents in NMR Imaging", in *FEBS Letters*, vol. 168, No. 1, Mar. 1984, pp. 70–74.

*Primary Examiner*—C. Fred Rosenbaum
*Attorney, Agent, or Firm*—Fish & Richardson

[57]            ABSTRACT

A method of decreasing the NMR relaxation times ($T_1$ or $T_2$) of water protons in contact with a biological tissue, the method involving administering to a human patient an NMR contrast agent comprising a paramagnetic ion complexed with a chelating substance, the contrast agent being characterized in that it is capable of binding non-covalently and non-immunologically to a component of the tissue, and as a result of such binding is capable of enhancing relaxivity of the water protons by a factor of at least 2, compared to the relaxivity induced by the paramagnetic substance alone free in solution, and subjecting the patient to NMR imaging.

11 Claims, No Drawings

VIVO ENHANCEMENT OF NMR RELAXIVITY

BACKGROUND OF THE INVENTION

This application is a continuation-in-part of Lauffer et al. U.S. Ser. No. 731,841, filed May 8, 1985.

This invention relates to diagnostic NMR imaging.

NMR imaging has been used in medical diagnosis for a number of years. The use of contrast agents to enhance its diagnostic utility has only recently appeared. For example, Gries et al. German Patent No. DE 3,129,906 describes NMR contrast agents which consist of a paramagnetic ion complexed with a chelating agent and a base or acid, e.g., the di-N-methylglucosamine salt of manganese chelated with EDTA.

SUMMARY OF THE INVENTION

The present invention provides an in vivo method of decreasing the NMR relaxation times of water protons in contact with a biological tissue. The method involves administering to a human patient an NMR contrast agent containing a paramagnetic metal ion complexed with a chelating substance, the contrast agent being characterized in that it is capable of binding non-covalently and non-immunologically to a component of the tissue, and as a result of such binding is capable of enhancing the relaxivity (i.e., decreasing the NMR relaxation times $T_1$ or $T_2$) of the water protons by a factor of at least 2, compared to the relaxivity induced in such water protons by the paramagnetic substance alone free in solution; and subjecting the patient to NMR imaging.

Preferably, the contrast agent has a specific affinity for the biological tissue in which binding occurs. (As used herein, "specific affinity" means capable of being taken up by, retained by, or bound to a particular tissue or tissue component to a substantially greater degree than other tissue or tissue components; agents which have this property are said to be "targeted" to the "target" tissue or component.)

The components to which the agents of the invention bind are generally particular chemical classes, e.g., proteins, lipids, or polysaccharides. It has been found that the tight binding of the agents to these components causes an increase (at least by a factor of 2) in the longitudinal ($1/T_1$) and transverse ($1/T_2$) relaxivity of water protons by the metal complex. Relaxivity enhancement is apparently due in large part to an alteration in the effective correlation time of the electron-nuclear interaction, as described in Lauffer et al. (1985) Magn. Res. Imaging 3, 11.

In the agents of the invention, the toxic paramagnetic ion (e.g., gadolinium) is strongly complexed by a chelating agent to reduce toxicity; it has been found that such agents are effective in reducing $T_1$ and $T_2$ (discussed below), despite the relatively lower accessibility of the paramagnetic ion to the surrounding water protons.

Examples of classes of chelating substances of the invention are porphyrins, cryptate compounds, and bis, tris, or tetra-catechol compounds.

The contrast agents of the invention which bind tightly to proteins are also taken up specifically by human hepatocytes, compared to human reticuloendothelial cells, and, because hepatocytes make up the bulk of the liver, provide superior NMR imaging of the liver. The agents thus allow visualization of hepatocarcinoma or metastatic tumors of the liver, whose cells take up the agents at a different rate, or retain the agent for a different length of time, than normally functioning hepatocytes. The invention also allows the use of NMR imaging to monitor liver function, as manifested by uptake or retention rates of the contrast agents of the invention.

Other features and advantages of the invention will be apparent from the following description of the preferred embodiments thereof, and from the claims.

DESCRIPTION OF THE PREFERRED EMBODIMENTS

Preferred embodiments of the invention are described below.

Properties of Contrast Agents

Many agents of the invention will have utility in a wide range of applications, because the chemical requirements for tight binding to many components are the same, and also because in some instances the same properties which induce tight binding also influence tissue specificity. For example, the properties of agents which cause selective uptake by hepatocytes compared to reticuloendothelial cells also cause tight binding of the agents to proteins, e.g., intracellular proteins of hepatocytes.

The preferred NMR contrast agents of the invention possess a number of physical/chemical properties, discussed below, related to their utility in diagnostic applications.

In order for agents which are targeted to provide the NMR contrast needed for imaging, they must alter the proton NMR relaxation time in the target component. Thus the agents must have properties which cause them to selectively be taken up by or bound to the target. This is achieved either by means of a higher rate of uptake of the contrast agent by the target, or by a different retention profile between target and non-target tissues. NMR contrast is achieved by the altering, by the paramagnetic portion of the agent, of $T_1$ (longitudinal relaxation time) or $T_2$ (transverse relaxation time) of the water protons in the target.

As mentioned above, one tissue component to which the agents of the invention can bind are proteins. These can be intracellular proteins, e.g., the proteins such as ligandin (also known as Y protein or glutathione-S-transferase (EC 2.5.1.18) and Protein A (also known as Z protein or fatty acid binding protein) inside hepatocytes (J. Clin. Invest. 48, 2156–2167 (1969)). Where the agents are targeted to particular cells such as hepatocytes, it is generally the cells, and not the intracellular proteins themselves, to which the agents are targeted as a result of the properties of the agents, which properties in turn cause tight binding to the intracellular proteins of those cells.

Agents which have protein-binding propeties can bind not only to intracellular proteins but also to serum proteins such as human serum albumin (HSA). This binding provides selective enhancement of intravascular structures or patterns on NMR images, permitting diagnosis of blood/brain barrier disruptions caused, e.g., by strokes and brain tumors, and also permitting flow imaging of the blood. For example, some agents can bind to both HSA and ligandin in vivo, and thus represent dual intravascular-hepatobiliary agents.

Another important protein which is bound tightly by the protein-binding agents is the immature, poorly cross-linked collagen present in tumors. This collagen can be bound tightly by NMR contrast agents which comprise a paramagnetic metal ion complexed with a porphyrin. When these proteins are bound, the agent serves the dual roles of tumor targeting and relaxivity enhancement.

Protein binding is provided for by the incorporation of hydrophobic groups into the agent, and providing the agent with the proper net charge.

Hydrophobic Binding

Binding is promoted when both the contrast agent and the protein contain one or more hydrophobic domains; the contrast agent binds non-covalently to the protein through Van der Waals interactions between the hydrophobic domains, thus enhancing binding.

Where the target is a protein, lipophilicity enhances binding of the contrast agents to the protein. Lipophilicity is provided by a non-polar structure, the presence of at least one aryl group (e.g., a substituted or unsubstituted phenyl ring), at least one halogen atom, and/or hydrophobic alkyl groups. For lipophilicity, it is also desirable that the contrast agent not carry excessive charge, i.e., of absolute value greater than 4, at physiological pH.

Lipophilicity is expressed in terms of octanol:water coefficient, determined by introducing a small amount ($<0.1$ mM) of the radiolabeled contrast agent into equal volumes of octanol and Tris buffer (50 mM, pH 7.4). The coefficient of the agents of the invention is preferably at least 0.005, and more preferably at least 0.01.

Another index related to lipophilicity is that of protein-binding. Binding capacity can be expressed as the percentage of the agent bound to 4.5% human serum albumin (HSA) at a concentration of 0.2 mM of the agent, as determined by equilibrium dialysis. For protein-targeted agents, preferably at least 15%, and more preferably at least 50%, of the agent, binds to HSA.

Electrostatic Interactions

Binding may be further increased if electrostatic interactions between the contrast agent and protein are possible. Thus, if the protein is known to have positively charged binding sites (e.g., human serum albumin) or if the protein is known to have the highest affinity for anionic ligands (e.g., albumin, ligandin or Protein A), then the net charge on the agent should be negative, preferably $-1$ to $-4$. Also, direct electrostatic interactions with positively charged residues may be promoted if the agent has additional negatively charged groups (e.g., sulfonate or carboxylate) that are not coordinated to the metal ion in solution.

Alternatively, if the binding sites are known to have anionic character, the agent should have overall positive charge.

Molecular Weight

The agents preferably have a molecular weight of at least 250, and more preferably over 300.

Solubility

To facilitate administration and uptake, the agents should have good water solubility, and preferably should be soluble to a concentration of at least 1.0 mM in normal saline at 20° C.

Relaxivity

The contrast agents of the invention must, as mentioned above, lower either $T_1$ or $T_2$ or both. The ability to achieve this is referred to as "relaxivity."

Relaxivity is optimal where the paramagnetic ion, when bound to the chelating ligand, still has one or more open coordination sites for water exchange. Generally, one or two such sites are preferred, since the presence of more than two open sites in general will unacceptably increase toxicity by release of the metal ion in vivo. However, zero open coordination sites may also be satisfactory, though not preferable, since second coordination sphere water molecules are still relaxed and binding-enhancement is still possible.

In vitro relaxivity is expressed in units of $s^{-1} mM^{-1}$, or change in $1/T_1$ or $1/T_2$ per mM agent, as measured in saline at 20 MHz. Preferably the agents have an in vitro relaxivity of at least $0.5 s^{-1} mM^{-1}$, more preferably at least $1.0 s^{-1} mM^{-1}$.

Relaxivity can also be measured in vivo for the tissue component of interest. In vivo relaxivity is expressed in units of $s^{-1} (\mu mol/gram\ of\ tissue)^{-1}$, representing the change in $1/T_1$ or $1/T_2$ above that of saline-injected controls caused by the agents, divided by the concentration of the agent (in $\mu mol/gram$ of tissue). Tissue concentration is measured using agents made with radiolabeled paramagnetic ions. Preferably, the in vivo relaxivity of the agents in liver tissue is at least $1.0 s^{31\ 1} (\mu mol/g)^{-1}$. The agents should bind sufficiently tightly to enhance relaxivity by a factor of at least 2. This increased relaxivity will allow for lower doses of the contrast agents and thus a higher margin of safety in their use.

To maximize the degree of relaxivity enhancement, it is desirable to maximize the rigidity of the binding interaction. Preferably, this is achieved by providing the contrast agent with at least one aryl or aliphatic group which makes multiple contacts with the biological binding site, preventing free rotation. Additionally, free (non-coordinating) charged groups (e.g., sulfonate or carboxylate) can be incorporated into the agent to promote electrostatic interactions with positively charged amino acid residues; this will increase both the binding affinity and rigidity.

A different strategy to increase the relaxivity of metal complexes is to alter the configuration of the donor atoms around the metal ions to achieve the most symmetrical orientation. This symmetry of the ligand field may lead to longer electron spin relaxation times, and higher relaxivities. The DOTA ligands for $Gd^{+3}$ (described below) are an example in which the symmetry is very high (almost cubic) compared to, e.g., DTPA-derived ligands (described below), which wrap around the metal ion in an anisotropic fashion. An additional benefit of symmetry-constrained macrocyclic ligands like DOTA is their high kinetic stability (vide infra).

Toxicity

The contrast agents must have acceptably low toxicity levels at the dosage required for contrast enhancement, and preferably have an $LD_{50}$ of at least 0.05 mmol/kg. Toxicity of the contrast agents is a function of both the inherent toxicity of the intact complex, and of the degree to which the metal ion dissociates from the chelating agent; toxicity generally increases with the degree of dissociation. For complexes in which kinetic stability is low, a high thermodynamic stability (a formation constant of at least $10^{15} M^{-1}$, and more preferably at least $10^{20} M^{-1}$) is desirable to minimize dissociation and its attendant toxicity. For complexes in which kinetic stability is comparatively higher, dissociation can be minimized with a lower formation constant, i.e., $10^{10}$ M$^-$or higher. Kinetically stable complexes generally contain a paramagnetic metal ion, e.g., gadolinium (III), complexed with a highly constrictive chelating agent, e.g., dibenzo-1, 4, 7, 10-tetraazacyclotetradecene 1, 4, 7, 10-tetraacetic acid (dibenzo-DOTA).

Toxicity is also a function of the number of open coordination sites in the complex; the fewer open coordination sites, the less tendency there is, generally, for the chelating agent to release the cytotoxic paramagnetic ion. Preferably, therefore, the complex contains two, one, or zero open coordination sites. The presence of one or even two open coordination sites can be acceptable in agents in which the paramagnetic substance has a high magnetic moment (i.e., is strongly paramagnetic), and can thus affect $T_1$ or $T_2$ at a low dosage; an example is gadolinium, which is strongly paramagnetic owing to its seven unpaired electrons.

The paramagnetic portion of the contrast agents of the invention can be any paramagnetic ion of the transition metal or lanthanide series which has at least one, and more preferably five or more, unpaired electrons, and a magnetic moment of at least 1.7 Bohr magneton. Suitable ions include gadolinium (III), iron (III), manganese (II and III), chromium (III), copper (II), dysprosium (III), terbium (III), holmium (III), erbium (III), and europium (III); most preferred are gadolinium (III), and iron (III), and manganese (II).

Chelating Ligand

The following discussion applies to chelating ligands which cause the agents of the invention to bind tightly to proteins and to be selectively taken up by functioning hepatocytes.

The organic chelating ligand should be physiologically compatible and preferably contains at least 1 aryl ring which may be substituted with halogen atoms and/or $C_1$–$C_{10}$ alkyl groups. The molecular size of the chelating ligand should be compatible with the size of the paramagnetic substance. Thus gadolinium (III), which has a crystal ionic radius of 0.938 Å, requires a larger chelating ligand than iron (III), which has a crystal ionic radius of 0.64 Å. Preferably, the chelating ligand is a single multidentate ligand. Such ligands maximize the stability of the contrast agents towards hydrolysis, and minimize the transfer of the metal ion from the contrast agent to binding sites on the target component.

One suitable class of chelating ligands are ethylene-bis-(2-hydroxyphenylglycine) ("EHPG"), and derivatives thereof, including 5-Cl-EHPG; 5-Br-EHPG; 5-Me-EHPG; 5-t-Bu-EHPG; and 5-sec-Bu-EHPG. EHPG and derivatives thereof have the structure:

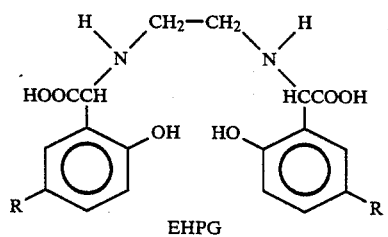

R = Cl, Br, I, CH$_3$, t-Bu, sec-Bu

Although substitution at the 5 position of EHPG is the most effective in increasing lipophilicity, substitution at any position on the two phenyl rings can be used.

Another suitable class of chelating ligands are benzodiethylenetriamine-pentaacetic acid (benzo-DTPA) and derivatives thereof, including dibenzo-DTPA; phenyl-DTPA; diphenyl-DTPA; benzyl-DTPA; and dibenzyl-DTPA. Two of these compounds have the structures shown below:

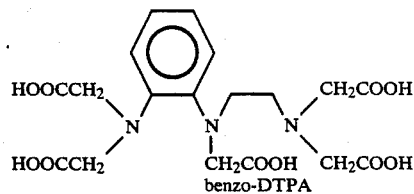

benzo-DTPA

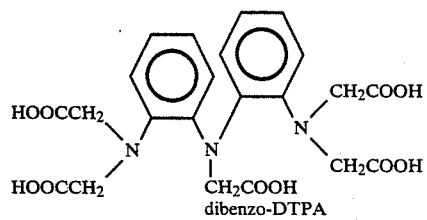

dibenzo-DTPA

Another class of suitable chelating ligands are bis-2 (hydroxybenzyl)-ethylene-diaminediacetic acid (HBED) and derivatives thereof. The structure of HBED is shown below:

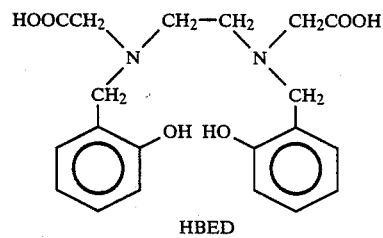

HBED

The HBED ligand advantageously has a very high formation constant for iron of $10^{40}$. This ligand is available from the Strem Chemical Company.

Another suitable class of chelating ligands is the class of macrocyclic compounds which contain at least 3 carbon atoms, more preferably at least 6, and at least two hetero (O and/or N) atoms. The macrocyclic compounds can consist of one ring, or two or three rings joined together at the hetero ring elements. One suitable class of mono-macrocyclic chelating ligands has the general formula

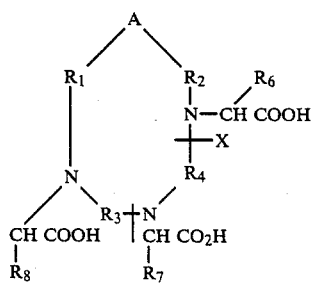

where A is —N— or

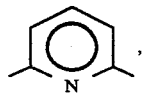

X is 0 or 1, each $R_5$, $R_6$, $R_5$—$CH_2CO_2H$ $R_7$, and $R_8$, independently, is ethyl, propyl, butyl, pentyl, or

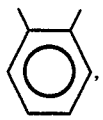

provided that when A is

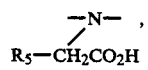

at least one R group must be

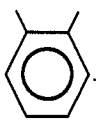

The aryl groups may be substituted with halogen atoms or $C_1$-$C_4$ alkyl groups. Examples of suitable macrocyclic ligands include benzo-DOTA, where DOTA is 1, 4, 7, 10-tetraazacyclotetradecane-1, 4, 7, 10-tetraacetic acid; dibenzo-DOTA; benzoz-NOTA, where NOTA is 1, 4, 7-triazacyclononane- N, N', N''''-triacetic acid; benzo-TETA, where TETA is 1, 4, 8, 11-tetraazacyclotetradecane-1, 4, 8, 11-tetraacetic acid; benzo-DOTMA, where DOTMA is 1, 4, 7, 10-tetraazacyclotetradecane-1, 4, 7, 10-tetra(methyl tetraacetic acid); and benzo-TETMA, where TETMA is 1, 4, 8, 11-tetraazacyclotetradecane-1, 4, 8, 11-(methyl tetraacetic acid).

Hydrophobicity, and thus lipophilicity, can also be provided, in the case of ligands (e.g., DOTA derivatives) containing ethylenediamine portions by attaching the above hydrophobic substituents directly to the ethylene carbon atoms. For example, DOTA has the structure:

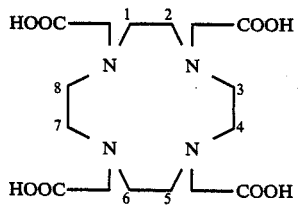

Hydrophobic substituents, e.g., fused phenyl rings or $C_1$-$5$ alkyl groups, can be attached to one or more of carbon atoms 1-8 of DOTA.

Another suitable class of chelating ligands are DTPA derivatives containing hydrophobic substituents. Structures of suitable such derivatives are given below, in which each $R_1$, $R_2$, $R_3$, $R_4$ and $R_5$, independently, can be a $C_{6-10}$ aryl group, e.g., phenyl or benzyl; or a $C_{1-5}$ aliphatic group, e.g., methyl or ethyl.

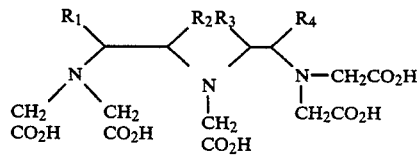

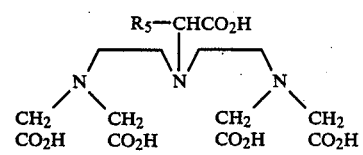

Another suitable class of chelating ligands are derivatives of 1,3-propylenediaminetetraacetic acid (PDTA) and triethylenetetraaminehexaacetic acid (TTHA), given below. Each $R_1$, $R_2$, $R_3$, $R_4$, $R_5$, $R_6$, and $R_7$ group, independently, can be a $C_{6-10}$ aryl group, e.g., phenyl or benzyl; or a $C_{1-5}$ aliphatic group, e.g., methyl or ethyl.

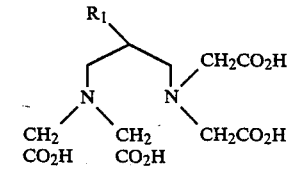

PDTA

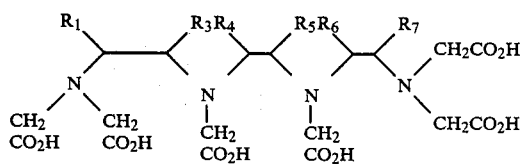

Another suitable class of chelating ligands are derivatives of 1,5,10-N,$N^1$,$N^{11}$-tris(2,3-dihydroxybenzoyl)-tricatecholate (LICAM) and 1,3,5-N,N',N''-tris(2,3-dihydroxybenzoyl)aminomethylbenzene (MECAM), having the structures given below. Each $R_1$, $R_2$, $R_3$, $R_4$, $R_5$, and $R_6$, independently, can be $CO_2H$, $SO_3H$, H, a halogen, e.g., Cl, or a $C_{1-5}$ alkyl group, e.g., methyl or ethyl.

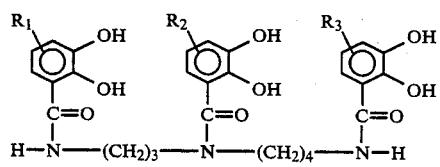

LICAM

-continued

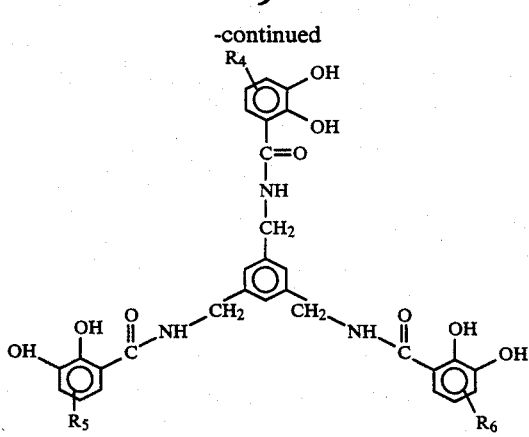

MECAM

Synthesis

The contrast agents of the invention can be synthesized from commercially available or readily synthesized reagents using conventional synthetic methods. In general, a salt of the paramagnetic ion is added to a slightly alkaline (pH 7.4–9) aqueous solution of the chelating ligand and the resulting mixture is stirred for 3–24 hours at room temperature. The resulting contrast agent is then used immediately or stored in lyophilized form or in physiological buffer until use.

The synthesis of iron (III)-(EHPG)$^-$ is carried out as follows. EHPG (Sigma) is dissolved at room temperature in distilled, deionized water maintained at pH 8–9 by addition of 1M NaOH. Solid FeCl$_3$.6H$_2$O is added to the solution and the pH adjusted to 7.4 with 1M NaOH. The resulting dark red solution is then stirred at room temperature for 30 minutes, after which it is filtered with 0.2 μm micropore filters (Gelman). The concentration of iron (III)-(EHPG)$^-$ is determined by visible absorption of diluted aliquots using a Beckman Spectophotometer and an extinction coefficient at 480 nm of 4300 CM$^{-1}$M$^{-1}$.

To make iron chelates of EHPG derivatives the first step is to make the appropriate EHPG derivative, according to Mannich reaction, described in Theodorakis et al. (1980) J. Pharm. Sci 69, 581; the reaction employs ethylenediamine, dichloroacetic acid, and the appropriate parasubstituted phenol. The reaction scheme for 5-Br-EHPG is:

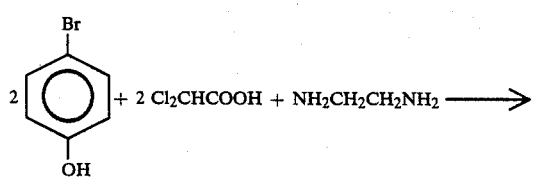

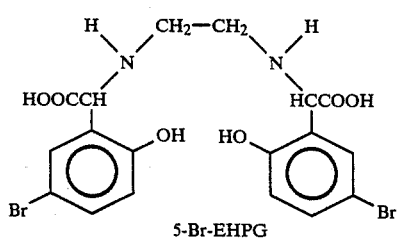

5-Br-EHPG

Iron (III)-(5-Cl-EHPG)$^-$, iron (III)-(5-Bu-EHPG)$^-$, iron (III)-(5-Me-EHPG)$^-$, and iron (III)-HBED are prepared in analogous fashion to iron-EHPG.

The structure of iron-EHPG is:

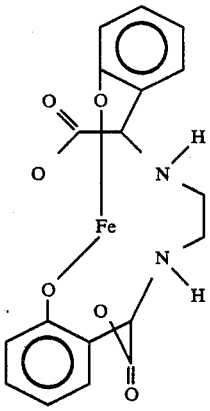

The octanol/water partition coefficients and HSA binding percentages of Iron-EHPG, Iron-(5-Br-EHPG), and Iron (HBED) are shown below:

|  | [octanol]/[water] | % bound to HSA |
| --- | --- | --- |
| Iron-EHPG | 0.013 | 17 |
| Iron-(5-Br—EHPG) | 0.89 | 82 |
| Iron-HBED | 0.050 | 34 |

The macrocyclic DOTA chelating ligands are synthesized generally as described in Desreux et al. (1984) Inorg. Chem. 19, 1319, generally according to the reaction

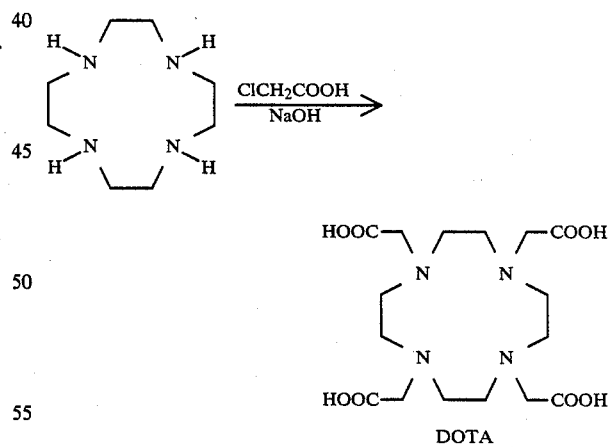

DOTA

DOTA itself lacks sufficient lipophilic groups for hepatocellular uptake. Two derivatives with the required lipophilicity (provided by fused phenyl rings), benzo-DOTA and dibenzo-DOTA, are made according to the following general reaction scheme. (Alternatively, hydrophobic substituents can be incorporated into, e.g., DOTA, via substituted ethylenediamines prepared according to Meares et al. (Anal. Biochem. 100 152–159 (1979).)

DTPA derivatives (e.g., benzo-DTPA and dibenzo-DTPA) are made by methods analogous to the methods used for making benzo-EDTA (McCandlish et al. (1978) Inorg. Chem. 17, 1383).
Paramagnetic ion chelating ligand complexes made using DOTA derivatives are made generally as described earlier, with a longer time (24 hours) and higher reaction temperatures being required for the formation of metal ion/macrocyclic ligand complexes. A reaction scheme is shown below:
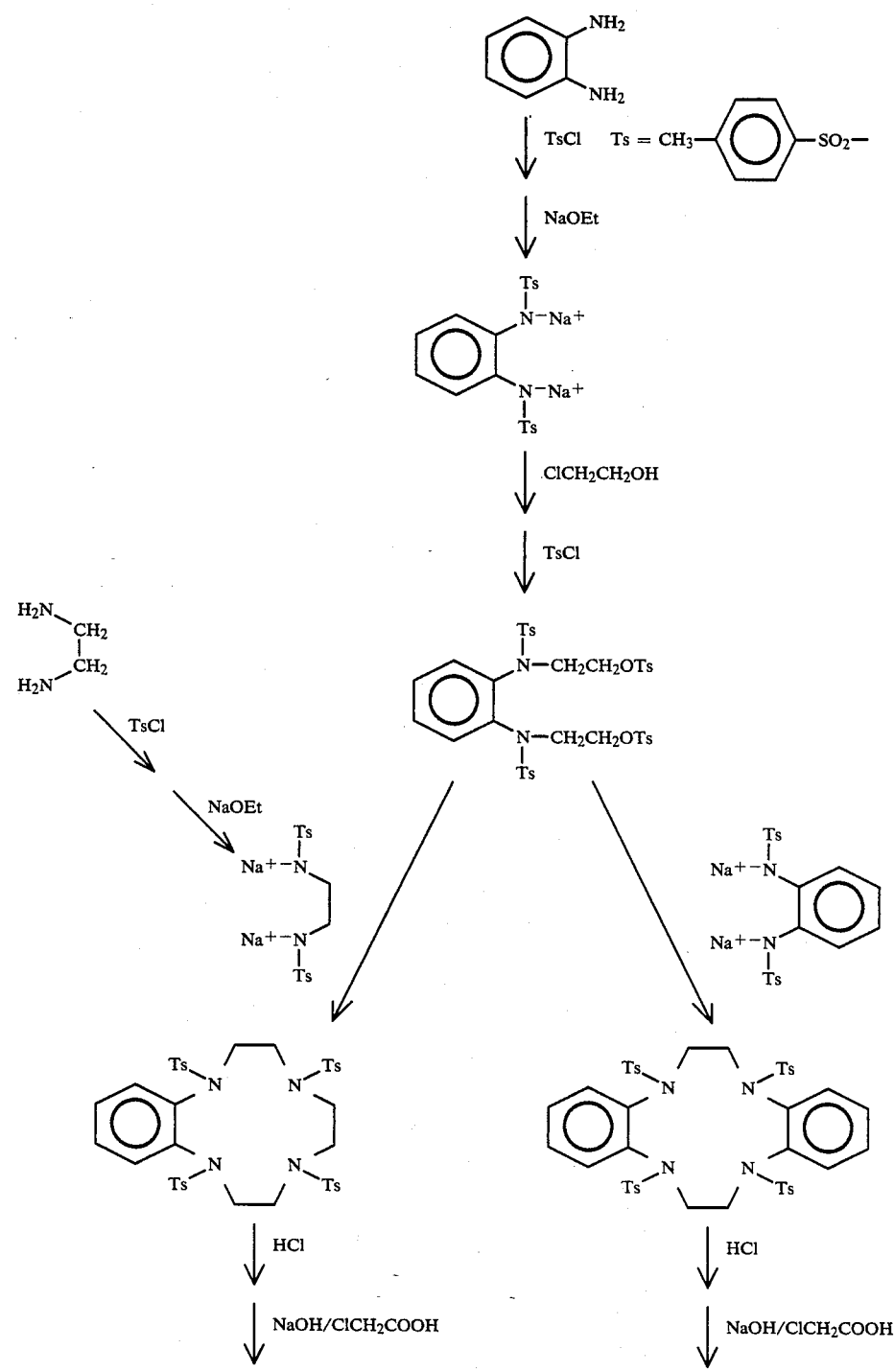

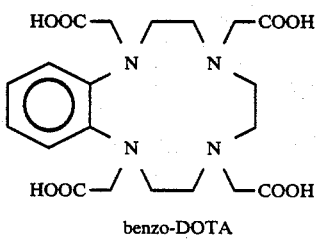
benzo-DOTA

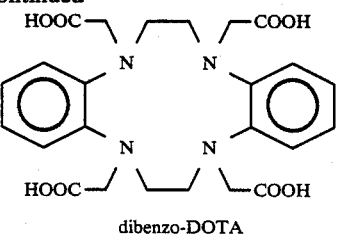
dibenzo-DOTA

Use

The contrast agents of the invention are administered orally or intravenously in physiological buffer. Dosage depends on the sensitivity of the NMR imaging instrumentation, as well as on the composition of the contrast agent. For example, a contrast agent containing a highly paramagnetic substance, e.g., gadolinium (III), generally requires a lower dosage than a contrast agent containing a paramagnetic substance with a lower magnetic moment, e.g., iron (III). In general, dosage will be in the range of about .001-1 mmol/kg, more preferably about 0.005-0.05 mmol/kg.

Following administration of the contrast agent, conventional NMR imaging is carried out; the choice of pulse sequence (inversion recovery, IR; spin echo, SE) and the values of the imaging parameters (echo time, TE; inversion time, TI; repetition time, TR) will be governed by the diagnostic information sought. In general, if one desires to measure $T_1$, then TE should be less than 30 milliseconds (or the minimum value) to maximize $T_1$ weighting. Conversely, if one desires to measure $T_2$, then TE should be greater than 30 milliseconds to minimize competing $T_1$ effects. TI and TR will remain approximately the same for both $T_1$- and $T_2$-weighted images; TI and TR are generally on the order of about 200-600 and 100-1000 milliseconds, respectively.

NMR Imaging Using Iron (III)-(EHPG)

Iron (III)-(EHPG)$^-$ was prepared as described above and used for in vivo imaging of rat livers as follows.

Fasted male Sprague-Dawley rats (of average weight of about 400g) were anesthetized with intraperitoneal pentobarbitol (50 mg/kg), placed on a calibrated carrier, and subjected to NMR imaging, along with calibration tubes containing paramagnetically-doped water or agar gels of known $T_1$ and $T_2$, to establish an initial baseline image. NMR imaging was performed with a horizontal bore (8cm) superconducting magnet system (Technicare Corp.) at a magnetic field strength of 1.4 tesla ($^1$H resonance of 61.4 MHz). Images were obtained using a 2-D Fournier transform technique with a slice selection determined by selective irradiation. All images were obtained using 128 phase encoded gradient steps. To maximize $T_1$ contrast, an IR pulse sequence was used (TE 15 msec, TI 400 msec, TR 1000 msec).

After baseline images were obtained, the rats were removed from the magnet and injected in the tail vein with 0.2 mmol/kg of iron (III)-(EHPG)$^-$. As a comparison, some rats received 0.2 mmol/kg of iron (III)-(DTPA)$^{-2}$ instead. The rats were then reinserted into the magnet, along with the calibration tubes, in the same position as for the initial baseline imaging. Imaging began immediately and continued for 1.5-3 hours. Background-subtracted, region-of-interest intensity values of liver and muscle were obtained for each image; these values were then normalized for any alteration in the signal intensity of the calibration tubes.

The IR 1000/400/15 images of rats which recieved iron (III)-(EHPG)$^-$ demonstrated a marked and prolonged increase in signal intensity of the liver consistent with a short $T_1$. In contrast, images of rats which received iron (III)-(DTPA)$^{-2}$ demonstrated only small and transient increases in liver intensity. This is presumably because, unlike iron (III)-(EHPG)$^-$, iron (III)-(DTPA)$^{-2}$ distributes throughout the extracellular liver space, rather than in functioning hepatocytes, and is rapidly excreted into the urine.

Ex vivo biodistribution studies measuring the $T_1$ and $T^2$ values of excised rat liver, blood, spleen, and thigh muscle at various post-injection times also demonstrated that iron (III)-(EHPG)$^-$ is predominantly taken up by functioning hepatocytes, and thus decreases the relaxation times of water protons in these cells.

Rats given intravenous doses of 2.0 mmol/kg of iron-EHPG suffered no apparent ill effects over a two-week observation period.

It is believed that the mechanism of operation of iron-EHPG is as follows. Relaxation time enhancement normally occurs where the unpaired electrons of the paramagnetic substance interact with water molecules directly bound to the paramagnetic substance; the degree of enhancement is inversely related to the distance from the paramagnetic center to the water molecules. In iron (III)-(EHPG)$^-$, however, there are no directly bound water molecules. Relaxation time enhancement, therefore, probably results mainly from the interaction between the paramagnetic substance and indirectly bound, second coordination sphere water molecules. It is believed that since there are a sufficiently large number of these outer-sphere water molecules, appreciable relaxation time enhancement occurs despite the larger distance between the water molecules and the paramagnetic substance.

Other embodiments are within the following claims.

I claim:

1. A method of decreasing the NMR relaxation times ($T_1$ or $T_2$) of water protons in contact with a biological tissue, said method comprising:

providing an NMR contrast agent which does not include an antibody and which comprises a paramagnetic ion selected from the group of ions consisting of gadolinium (III), iron (III), manganese (II and III), chromium (III), copper (II), dysprosium (III), terbium (III); holmium (III), erbrium (III) and europium (III), complexed with a chelating substance having at least one aryl ring which may be substituted in one or more positions with members of the group consisting of the halogens and the $C_1$-$C_{10}$ alkyl groups, said contrast agent being characterized in that it is capable of binding noncovalently to ligandin, or Protein A, or HSA of said tissue and as a result of such binding is capable of enhancing relaxivity of said water protons by a factor of at least 2, compared to the relaxivity induced by said paramagnetic substance alone free in solution, administering said NMR contrast agent to a human patient, and subjecting said patient to NMR imaging.

2. The method of claim 1 wherein the chelating substance is selected from the group consisting of ethylene-bis-(2-hydroxyphenylglycine) and its derivatives having the structure:

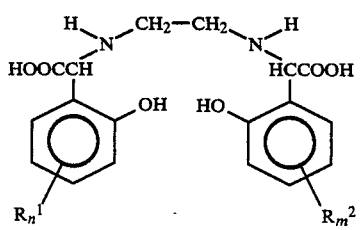

wherein each n and m, independently, is an integer between 0 and 4 inclusive, and each $R^1$ and $R^2$, independently, is Cl, Br, I, $CH_3$, t-Bu, or sec-Bu.

3. The method of claim 1 wherein the chelating substance is selected from the group consisting of benzodiethylenetriamine-pentaacetic acid and its derivatives having the structures:

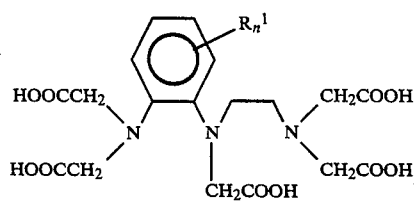

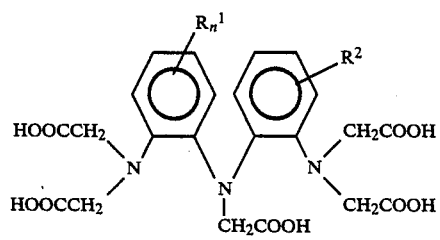

wherein n is an integer between 0 and 4 inclusive, and each $R^1$ independently, can be Cl,Br,I,$CH_3$, t-Bu or sec-Bu and $R^2$, independently, can be benzo, benzyl or phenyl.

4. The method of claim 1 wherein the chelating substance is selected from the group consisting of bis-2(hydroxybenzyl)-ethylene-diaminediacetic acid and its derivatives having the structure:

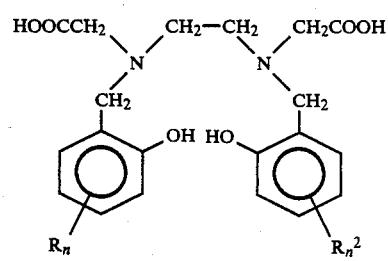

wherein each n and m, independently, is an integer between 0 and 4 inclusive, and each $R^1$ and $R^2$, independently, can be Cl, Br, I, $CH_3$, t-Bu, or sec-Bu.

5. The method of claim 1 wherein the chelating substance is selected from the group consisting of mono- and multi-macrocyclic compounds having between 3 and 6 carbon atoms and at least two hetero atoms from the group of O and N, wherein the mono-macrocyclic compounds have the general structure:

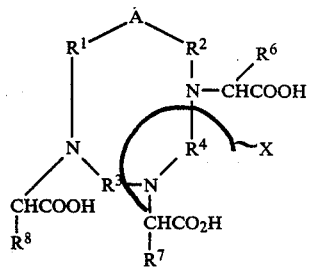

wherein: A can be

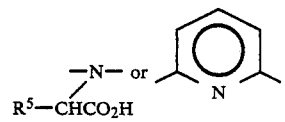

X, independently, is an integer between 0 and 1, inclusive, and $R^5,R^6,R^7$, and $R^8$, independently can be H or methyl and $R^1,R^2,R^3$ and $R^4$, independently, can be ethyl, propyl, butyl, pentyl or

provided that when A is

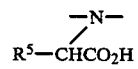

at least one R must be

and wherein said aryl groups may be substituted with halogen atoms or $C_1$-$C_4$ alkyl groups.

6. The method of claim 1 wherein the chelating substance is selected from the group consisting of derivatives of diethylenetriamine-penta acetic acid having the structure

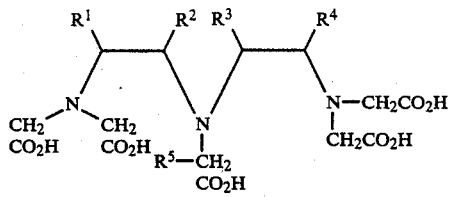

wherein $R^1$, $R^2$, $R^3$, $R^4$ and $R^5$, independently can be a $C_{6-10}$ aryl or $C_{1-5}$ aliphatic.

7. The method of claim 1 wherein the chelating substance is from the group of substances consisting of derivatives of 1,3 - propylenediaminetetraacetic acid having the structure:

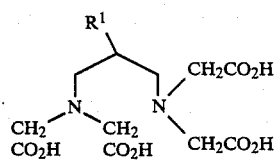

wherein $R^1$ can be $C_{6-10}$ aryl or $C_{1-5}$ aliphatic.

8. The method of claim 1 wherein the chelating substance is from the group of substances consisting of derivatives of triethylenetetraaminehexacetic acid having the structure:

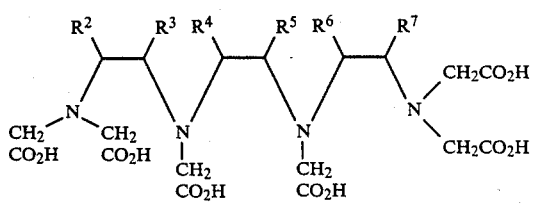

wherein $R^2$, $R^3$, $R^4$, $R^5$, $R^6$ and $R^7$, independently can be $C_{6-10}$ aryl or $C_{1-5}$ aliphatic.

9. The method of claim 1 wherein the chelating substance is from the group of substances consisting of derivatives of 1,5,10-N,N',N''-tris(2,3-dihydroxybenzoyl)-tricatecholate having the structure:

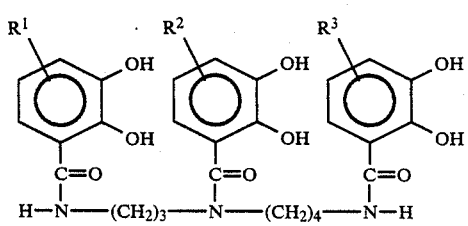

wherein each $R^4$, $R^5$ and $R^6$, independently, can be $CO_2H$, $SO_3H$, H, Cl, Br, I, or $C_{1-5}$ alkyl.

10. The method of claim 1 wherein the chelating substance is from the group of substances consisting of: derivatives of 1,3,5-N,N',N''-tris(2, 3-dihydroxybenzoyl)-aminomethylbenzene having the structure:

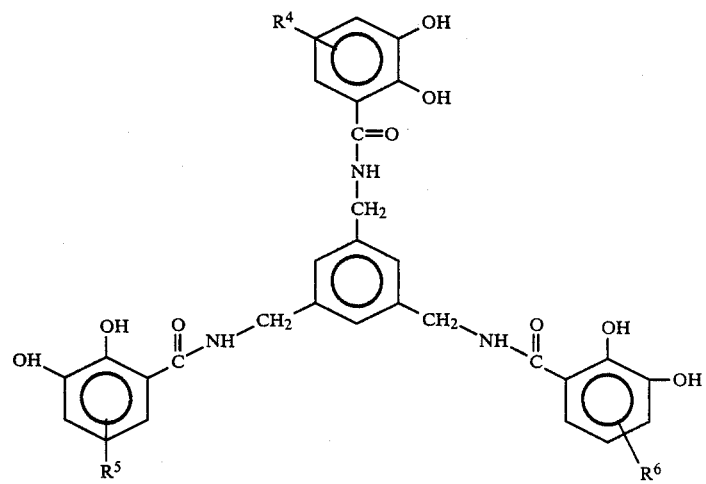

wherein each $R^4$, $R^5$, and $R^6$, independently, can be $CO_2H$, $SO_2H$, H, Cl, Br, I, or $C_{1-5}$ alkyl.

11. The method of claim 1 wherein the chelating substance is a derivative of 1, 4, 7, 10-tetraazocyclotetradecane-1,4,7,10-tetraacetic acid containing hydrophobic substituents attached to one or more of carbon atoms 1–8, said substituents being $C_{6-10}$ aryl groups e.g., phenyl or benzyl, or $C_{1-5}$ aliphatic, e.g., methyl or ethyl.

* * * * *

UNITED STATES PATENT AND TRADEMARK OFFICE
CERTIFICATE OF CORRECTION

PATENT NO. : 4,880,008

DATED : November 14, 1989

INVENTOR(S) : Randall B. Lauffer

It is certified that error appears in the above-identified patent and that said Letters Patent is hereby corrected as shown below:

Col. 4, line 24, "$S^{31}\ 1$" should read --$S^{-1}$--.
Col. 5, line 1, "M-" should read --$M^{-1}$--.
Col. 7, line 7, after "is", insert --H or methyl, and each $R_1$, $R_2$, $R_3$, and $R_4$, independently, is--.
Col. 7, line 20, in the formula, delete the "2" in "$CH_2$".
Col. 7, line 35, "benzoz-NOTA" should be --benzo-NOTA--.
Col. 7, line 36, "N, N', N'''' " should read --N, N', N''--.
Col. 8, lines 40, in the second formula, please substitute "$R_2$" in the place of "$R_1$" as shown below:

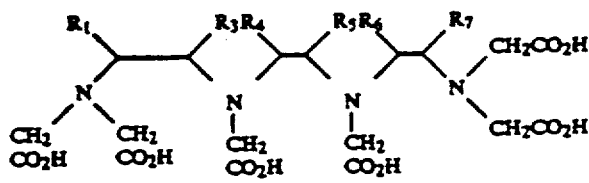

should be

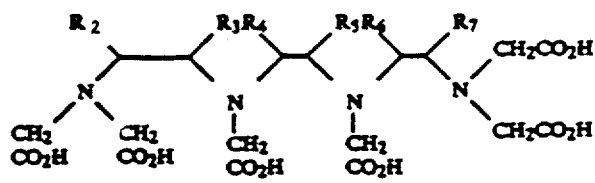

UNITED STATES PATENT AND TRADEMARK OFFICE
CERTIFICATE OF CORRECTION

PATENT NO. : 4,880,008

DATED : November 14, 1989

INVENTOR(S) : Randall B. Lauffer

It is certified that error appears in the above-identified patent and that said Letters Patent is hereby corrected as shown below:

Col. 10, lines 5-20, please correct the structure as shown by the formula below:

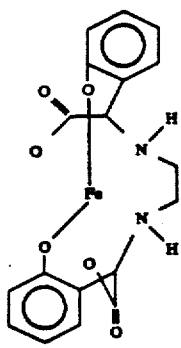   should be   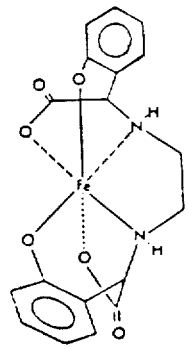

Col. 16, line 15, "Ch3" should read --$CH_3$--;

UNITED STATES PATENT AND TRADEMARK OFFICE
CERTIFICATE OF CORRECTION

PATENT NO. : 4,880,008

DATED : November 14, 1989

INVENTOR(S) : Randall B. Lauffer

It is certified that error appears in the above-identified patent and that said Letters Patent is hereby corrected as shown below:

Col. 17, line 14, in the structure, delete the "2" in "CH2" as shown in the formula below:

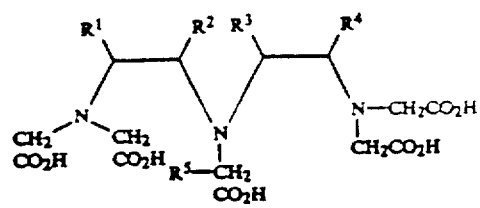 should be 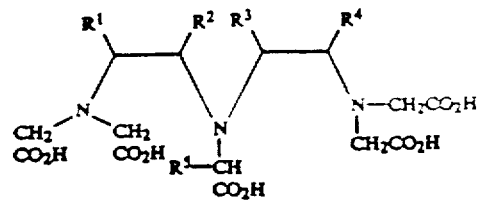

Signed and Sealed this

Twenty-first Day of July, 1992

*Attest:*

DOUGLAS B. COMER

*Attesting Officer*     *Acting Commissioner of Patents and Trademarks*

UNITED STATES PATENT AND TRADEMARK OFFICE
CERTIFICATE OF CORRECTION

PATENT NO. : 4,880,008

DATED : November 14, 1989

INVENTOR(S) : RANDALL B. LAUFFER

It is certified that error appears in the above-identified patent and that said Letters Patent is hereby corrected as shown below:

Column 1:
After the title of this invention and before "BACKGROUND OF THE INVENTION" --This invention was made with government support under CA07671 and CA42430 awarded by the National Cancer Institute of the National Institutes of Health. The government has certain rights in the invention." should be inserted.

Signed and Sealed this

Eighth Day of September, 1992

Attest:

DOUGLAS B. COMER

*Attesting Officer*　　　*Acting Commissioner of Patents and Trademarks*